United States Patent
Marks

Patent Number: 5,542,933
Date of Patent: Aug. 6, 1996

[54] CATHETER VALVE

[76] Inventor: Ronald Marks, 1124 Townsley Ave., Bakersfield, Calif. 93304

[21] Appl. No.: 14,774

[22] Filed: Feb. 8, 1993

Related U.S. Application Data

[62] Division of Ser. No. 898,035, Jun. 15, 1992, abandoned.

[51] Int. Cl.⁶ ........................................ A61M 5/00
[52] U.S. Cl. ..................... 604/188; 604/249; 604/236; 604/33; 604/167
[58] Field of Search ................... 604/188, 249, 604/236, 33, 213, 215, 110, 165, 158, 167, 168, 169

[56] References Cited

U.S. PATENT DOCUMENTS 2,413,303  12/1946  Folkman ................... 604/135
3,375,823   4/1968  Pamplin et al. ............ 128/200.19
4,560,373  12/1985  Sugino et al. ............. 604/30

*Primary Examiner*—C. Fred Rosenbaum
*Assistant Examiner*—V. Alexander
*Attorney, Agent, or Firm*—Mark Miller

[57] ABSTRACT

A valve for controlling the flow of fluids through a cannula or catheter made up of a single block piece in the shape of a backward "7" having a head and a stem. As the stem is raised in relation to the hub of the cannula or catheter, the head blocks any flow through the cannula or catheter; as the stem is lowered, the head retracts allowing the flow to continue.

1 Claim, 1 Drawing Sheet

CATHETER VALVE

This is a divisional of application Ser No. 07/898,035 filed on Jun. 15, 1992, now abandoned.

BACKGROUND OF THE INVENTION

The present invention relates generally to a valve for controlling the backflow of blood through an intravenous or arterial cannula or catheter in order to block the cannula or catheter so that there will be no blood loss while connecting tubing to the cannula or catheter.

SUMMARY OF THE INVENTION

Numerous existing arterial and intravenous cannulas or catheters do not utilize any method of stopping blood loss other than pressure on the artery or vein of the patient. Such methods increase the possibility of spreading disease and promote unnecessary blood loss. The present invention provides a simple valve that may be attached to the hub of a cannula or catheter to restrict the flow of fluids therethrough by a simple raising or lowering action. Pulling the stem of the present invention up causes a head attached thereto to move into position and completely block the cannula or catheter passageway, stopping the flow of fluid (blood). Pushing the stem of the present invention down causes the head to move out of the way allowing the flow to resume.

The invention is designed so that a hypodermic needle may be pushed through the catheter such that when the needle comes into contact with the head of the valve (presently blocking any flow) it causes the head to move aside, allowing the flow to continue, and the medicine or other material in the needle to be introduced into the catheter.

It is therefore a primary object of the present invention to provide a simple valve for use in intravenous or arterial cannulas or catheters.

It is also an important object of the present invention to provide a simple catheter valve that may be opened by means of the pressure resulting from a needle coming into contact with the head of the valve.

It is also an object of the present invention to provide a valve for use on intravenous or arterial cannulas or catheters that avoids blood loss and helps reduce the spread of disease.

DETAILED DESCRIPTION OF THE DRAWINGS

Figure 1:
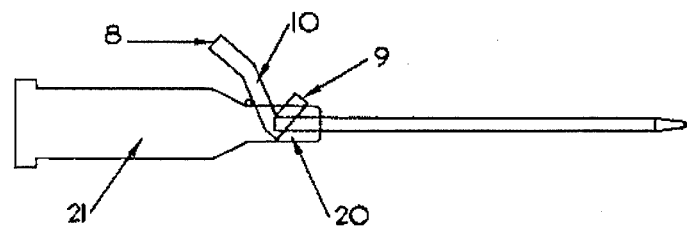
FIG. 1 is a side cutaway view of the invention in a closed state in place on a catheter.
Figure 2:
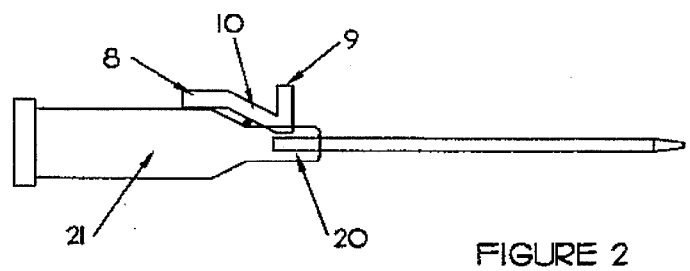
FIG. 2 is a side cutaway view of the invention in an open state in place on a catheter.
Figure 3:
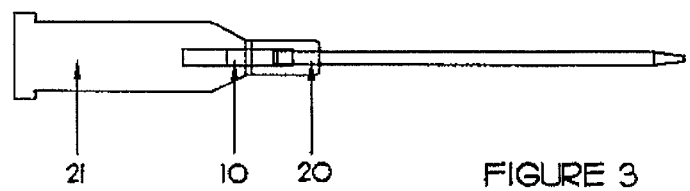
FIG. 3 is a perspective view of the invention in place on a catheter.
Figure 4:
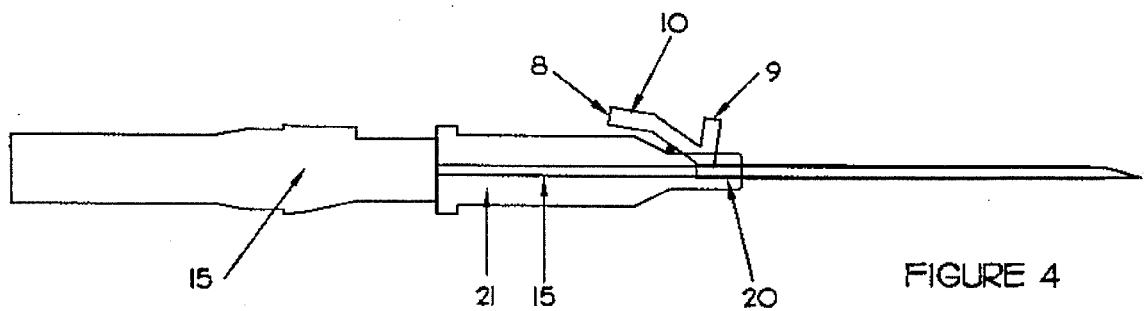
FIG. 4 is a side cutaway view of a needle pushing the invention open inside a catheter.

Referring to the drawings wherein like reference characters designate like or corresponding parts throughout the several views, and referring particularly to FIGS. 1, 2, and 4 it is seen that the invention includes a valve member 10 in the shape of a backward "7" including a head 9 and a stem 8. The valve member 10 is fitted into the side of a catheter hub 21 (as seen in FIG. 1) so that the head 9 protrudes into the bore of the catheter 20. When stem 8 is pushed down, the head 9 moves out of the way of the flow through the catheter 20 as seen in FIG. 2. When stem 8 is pulled up, head 9 blocks the bore of the catheter as seen in FIG. 3. A needle 15 may be pushed through a catheter as shown in FIG. 4 and force the head 9 out of the way in order to administer medication. When the needle is removed, stem 8 need only be pulled up to again block the flow.

DESCRIPTION OF THE PREFERRED EMBODIMENTS

In the preferred embodiment, the present invention is constructed of rigid plastic or the like, and is mounted on the hub of a cannula or catheter. It may also be mounted on the body of a syringe. The valve is in the shape of a backward "7" so that the top of the "7" is the head which blocks fluid flow, and the side of the "7" is the stem which is used to move the head and thereby open and close the valve. The shape of a backward "7" is important in that it allows the head to be moved aside by an incoming needle, so that medication or other material may be introduced into a catheter equipped with the valve without blood or fluid loss.

When the stem is pulled up, the head blocks the flow. When the stem is pushed down, either from the outside or by a needle entering the catheter or cannula, the head is moved aside and flow may resume.

I claim:

1. A blood vessel entry device comprising a catheter with a proximal end having a hub thereon, a distal end which enters a blood vessel, and a bore through which blood flows and which may receive a needle, and a valve attached to said catheter hub for controlling blood flow through said catheter said valve being in a block shape with a head at one end and a stem at an opposite end wherein said valve may be closed by said stem being raised manually be a user grasping said stem which action lowers said head into said catheter bore blocking blood flow through said catheter bore, wherein said valve may be opened by said stem being lowered manually by a user grasping said stem which action raises said head, allowing blood flow through said catheter bore wherein said valve may also be opened by a needle passing through said catheter bore, said needle coming into contact with said lowered head and raising said head, allowing blood flow through said catheter.

* * * * *